(12) United States Patent
Olson, Jr. et al.

(10) Patent No.: US 11,648,138 B2
(45) Date of Patent: May 16, 2023

(54) CATHETER WITH TAPERED COMPLIANT BALLOON AND TAPERED STENT

(71) Applicant: Abbott Cardiovascular System Inc., Santa Clara, CA (US)

(72) Inventors: Stephen Craig Olson, Jr., Temecula, CA (US); Senthil Eswaran, Sunnyvale, CA (US); Erik Eli, Redwood City, CA (US)

(73) Assignee: Abbott Cardiovascular System Inc., Santa Clara, CA (US)

( * ) Notice: Subject to any disclaimer, the term of this patent is extended or adjusted under 35 U.S.C. 154(b) by 178 days.

(21) Appl. No.: 17/322,631

(22) Filed: May 17, 2021

(65) Prior Publication Data

US 2021/0275332 A1 Sep. 9, 2021

Related U.S. Application Data

(63) Continuation of application No. 15/900,116, filed on Feb. 20, 2018, now abandoned.

(51) Int. Cl.
*A61F 2/958* (2013.01)
*A61F 2/915* (2013.01)
(Continued)

(52) U.S. Cl.
CPC ............... *A61F 2/958* (2013.01); *A61F 2/89* (2013.01); *A61F 2/915* (2013.01); *A61M 25/1002* (2013.01); *A61F 2002/91533* (2013.01); *A61F 2002/91575* (2013.01); *A61F 2210/0076* (2013.01); *A61F 2250/0039* (2013.01); *A61M 2025/1088* (2013.01); *A61M 2205/0216* (2013.01)

(58) Field of Classification Search
CPC .. A61F 2/958; A61F 2/89; A61F 2/915; A61F 2002/91575; A61M 25/1002; A61M 2250/0039; A61M 2025/1088; A61M 2205/0216
See application file for complete search history.

(56) References Cited

U.S. PATENT DOCUMENTS 5,334,146 A 8/1994 Ozasa
5,645,560 A * 7/1997 Crocker ............ A61M 25/1029
606/108

(Continued)

*Primary Examiner* — Sarah A Simpson
(74) *Attorney, Agent, or Firm* — Fulwider Patton LLP

(57) ABSTRACT

A balloon comprising: a center portion having a proximal end, a distal end opposite the proximal end, and a length between the proximal end and the distal end. The center portion comprises: a first nominal diameter and a first radial modulus at the proximal end; a second nominal diameter and a second radial modulus at the distal end; further wherein, the first nominal diameter is equal to the second nominal diameter, such that, when the balloon is inflated to a nominal pressure, the center portion has a constant diameter over the length; and further wherein, the first radial modulus is smaller than the second radial modulus, such that, when the balloon is inflated above a nominal pressure, the center portion adopts a tapered shape in which the proximal end has a first stretched diameter and the distal end has a second stretched diameter, the first stretched diameter being larger than the second stretched diameter.

2 Claims, 8 Drawing Sheets

(51) Int. Cl.
    *A61M 25/10*    (2013.01)
    *A61F 2/89*     (2013.01)

(56) References Cited

U.S. PATENT DOCUMENTS

| | | |
|---|---|---|
| 6,251,094 B1 | 6/2001 | Bleam |
| 6,258,108 B1 | 7/2001 | Lary |
| 6,273,910 B1 | 8/2001 | Limon |
| 6,290,485 B1 | 9/2001 | Wang |
| 7,105,015 B2 * | 9/2006 | Goshgarian ............. A61F 2/958 |
| | | 623/1.11 |
| 8,262,720 B2 | 9/2012 | Bonsignore et al. |
| 2002/0156523 A1 | 10/2002 | Lau et al. |
| 2006/0135983 A1 | 6/2006 | Melsheimer et al. |
| 2009/0312828 A1 | 12/2009 | Vrba |
| 2016/0184079 A1 * | 6/2016 | Scutti ...................... A61F 2/915 |
| | | 623/1.13 |
| 2019/0133799 A1 * | 5/2019 | Liang ...................... A61L 31/06 |

* cited by examiner

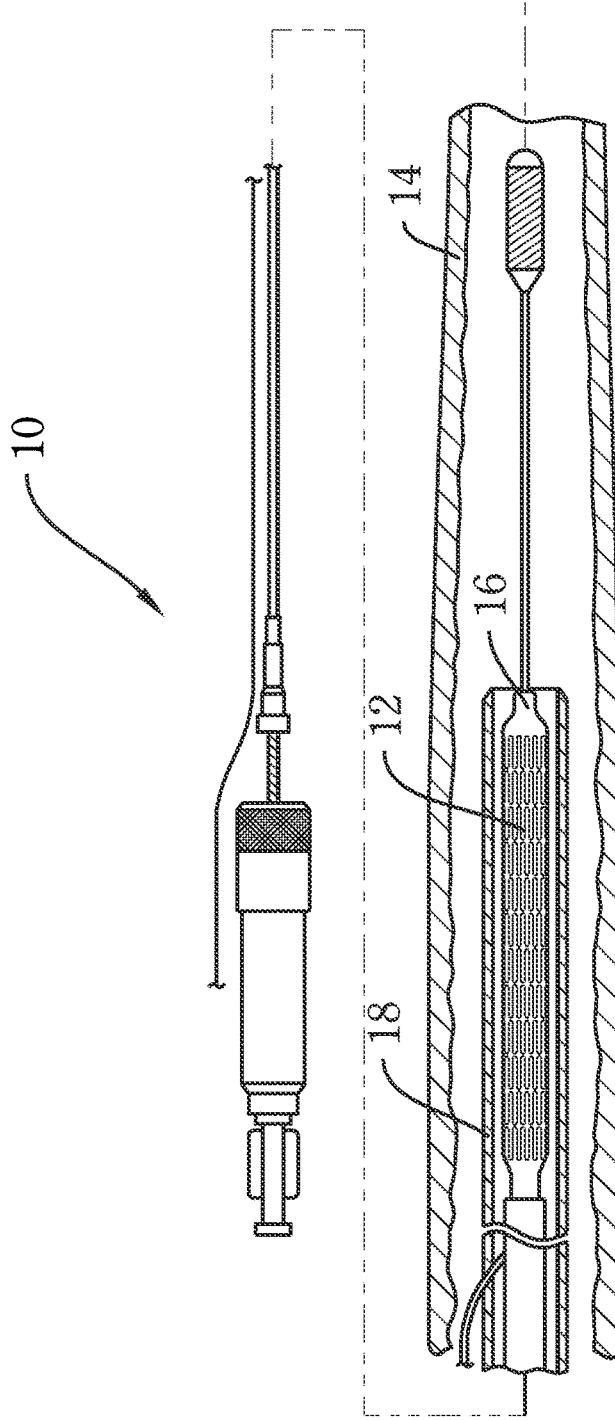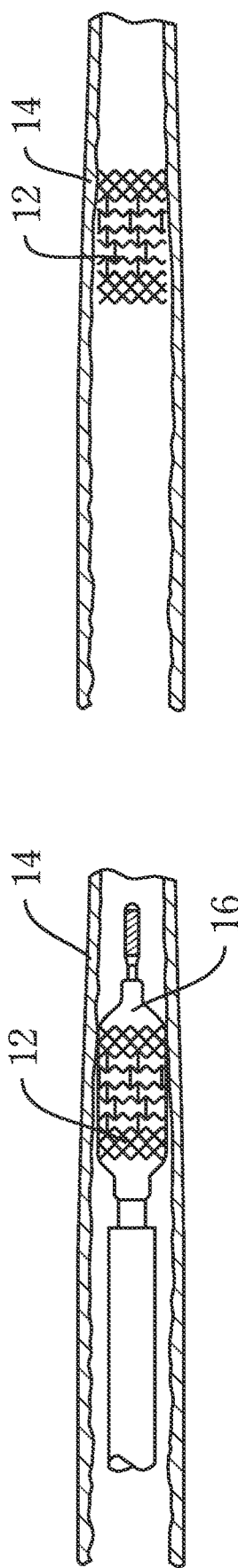
FIG. 1A (Prior Art)
FIG. 1B (Prior Art)
FIG. 1C (Prior Art)

Proximal ← → Distal

CATHETER WITH TAPERED COMPLIANT BALLOON AND TAPERED STENT

CROSS-REFERENCES TO RELATED APPLICATIONS

This is a continuation based on U.S. Ser. No. 15/900,116, filed Feb. 20, 2018, the contents of which is incorporated by reference herein in its entirety.

BACKGROUND

This application relates to balloon catheters for medical purposes such as angioplasty and stent delivery, and to stents suitable for delivery with such catheters.

Balloon catheters are well known in the art. Balloon catheters have been developed for various purposes including angioplasty, stent delivery, and many other applications in which medical devices must be expanded within a body cavity of a patient. The balloon is inserted inside the medical device on the tip of a catheter, and when the device has been successfully introduced into a body cavity via the vasculature of the patient, the balloon is expanded by a fluid medium transmitted via a lumen in the catheter. The expanding balloon expands the device by an amount that can be adjusted by the operating physician through visualization means such as fluoroscopy. FIG. 1 shows a known catheter system 10, which is tipped by a balloon 16 at its distal end upon which a stent 12 is mounted for delivery. A sheath 18 may cover the stent/balloon combination during delivery, and may be withdrawn prior to deployment of the stent 12.

Balloons on catheters have been provided with various properties. Some balloons have been configured to be compliant, which is to say, elastic. Under such structure, the greater the internal pressure, the greater the diameter of the expanded balloon. Some balloons have been configured to be non-compliant, which is to say inelastic. Such inelastic balloons have substantially only one expanded diameter, so that the operating physician can be assured that when the device is implanted, it will assume only one final diameter under a range of pressures.

However, in some procedures, it is desired by a physician for a balloon to assume a non-uniform diameter. Such a situation may arise where a stent having a substantial length is to be implanted in a vessel. While most vessels show no appreciable taper over a short length such as over 20 mm-30 mm, it is common for a vessel to taper appreciably over a substantial length, such as for example from 40 mm-80 mm. Specifically, the coronary artery lumen has unique character. It is well-known that the left anterior descending (LAD) artery diameter is typically not constant, and that it typically tapers narrower in its distal course. This is in comparison with the right coronary artery (RCA) which is more cylindrical over its course. It is estimated that the LAD loses 15% of its diameter for every 30 mm in its length.

FIGS. 1A-1C show a catheter with a balloon/stent mounted at a distal tip, in a body lumen 14 of a patient that tapers narrower along its distal course. In cases where a physician wishes to implant a stent having substantial length, the physician may be confronted by one or both of two problems. First, the physician may initially conclude that he/she is confronted with an artery that is substantially tubular with a constant diameter over the length. Therefore, he/she may select a balloon/stent capable of achieving a substantially tubular shape over the length. However, as she proceeds to deploy the stent, it may become apparent that the artery does in fact possess a taper along its length. Where, as in the case of a left anterior descending artery, the taper is 15% it will be appreciated that the cone angle of taper is 8 degrees. It is therefore quite possible that the surgeon discovers during deployment that the artery is in fact substantially tapered.

The problem that then may arise is that, having chosen a balloon/stent combination having a constant diameter, it may transpire that it is sized correctly at the proximal end in an expanded condition, but is too large at the distal end. Alternatively, he/she may be left with a constant diameter balloon/stent that is correctly sized at the distal end but is too small at the proximal end. This latter condition is exemplified in FIGS. 2 and 3. Thus, the physician, hoping to implant a substantially long stent that is uniformly shaped along its length and placed on a balloon having a uniform expanded shape along its length, may be compelled to compromise, and size the final expanded diameter to fit the vessel in the middle of the stent, and have a proximal end that is too small and a distal end that is too large for the vessel.

It is known how to impart an actual taper to a balloon. Typically, such is accomplished by imparting an initially tapered shape at the molding stage, and then upon inflation by expansion medium, the balloon adopts a tapered shape at nominal pressure, and continues to possess a tapered shape throughout the inflation process. This type of balloon however does not give the physician a choice of inflating the balloon to a uniform diameter at nominal pressure in the event that a uniform vessel is encountered, and then, in the event that it turns out that the vessel is tapered, to continue to inflate the balloon beyond nominal pressure to increase the diameter of the balloon only at the proximal end, while leaving the diameter of the balloon substantially unchanged at the distal end—thereby producing a suitable tapered balloon.

Thus there is a need in the art for a balloon that expands to a constant diameter at nominal pressure, but which expands to a tapered diameter in excess of nominal pressure. The present invention addresses these and other needs.

A corollary need in the art is for a stent that is suitable for use in conjunction with any of the balloons described herein.

The present invention addresses these, and other needs.

SUMMARY OF THE INVENTION

In one embodiment, the invention is a balloon for attachment to a distal portion of a medical catheter. The balloon comprises a center portion having a proximal end, a distal end opposite the proximal end, and a length between the proximal end and the distal end. The center portion further comprises a first nominal diameter and a first radial modulus at the proximal end; and a second nominal diameter and a second radial modulus at the distal end. The first nominal diameter is equal to the second nominal diameter, such that, when the balloon is inflated to a nominal pressure, the center portion has a constant diameter over the length. Furthermore, the first radial modulus is smaller than the second radial modulus, such that, when the balloon is inflated above a nominal pressure, the center portion adopts a tapered shape in which the proximal end has a first stretched diameter and the distal end has a second stretched diameter, the first stretched diameter being larger than the second stretched diameter.

In some embodiments, the center portion comprises a compliant polymer membrane which has a first thickness at the proximal end and a second thickness at the distal end, wherein the first thickness is less than the second thickness.

In other embodiments, the center portion comprises a compliant polymer membrane. A plurality of successive threads are wrapped circumferentially around the center portion to reinforce the center portion, the threads being spaced along the center portion at a constant pitch and being adhesively attached to the center portion. Further, an initial successive thread is located at the proximal end and has a first cross sectional area. A final successive thread is located at the distal end and has a second cross sectional area. A medial successive thread is located between the initial successive thread wherein the final successive thread has a third cross sectional area. Further, the first cross sectional area is smaller than the second cross sectional area and the third cross sectional area is larger than the first cross sectional area but smaller than the second cross sectional area. In further embodiments, the center portion comprises a compliant polymer membrane. An initial two consecutive threads are located at the proximal end and have a first pitch between them; a final two consecutive threads are located at the distal end and have a second pitch between them; and a medial consecutive two threads are located between the initial two consecutive threads and the final two consecutive threads and have a third pitch between them, wherein the first pitch is larger than the second pitch and the third pitch is smaller than the first pitch but smaller than the third pitch. In yet further embodiments, the center portion comprises a compliant polymer membrane. A first thread is wound in a helix along the center portion and a first two successive windings are located at the proximal end and have a first pitch. A final two successive windings are located at the distal end and have a second pitch, and a medial two successive windings are located between the first two successive windings and the final two successive windings and have a third pitch. The first pitch is larger than the second pitch and the third pitch is smaller than the first pitch but larger than the third pitch.

In yet a further embodiment, the center portion comprises a compliant polymer membrane. An initial successive thread is located at the proximal end and is formed from a material having a first elastic modulus. A final successive thread is located at the distal end and is formed from a material having a second elastic modulus. A medial successive thread is located between the initial successive thread and final successive thread, and is formed from a material having a third elastic modulus. The first elastic modulus is smaller than the second elastic modulus and the third elastic modulus is larger than the first elastic modulus but smaller than the second elastic modulus.

In another embodiment, the invention is a stent for insertion into a vessel of a patient. The stent comprises a plurality of rings that are successively connected to each other by a plurality of links, the plurality of rings extending in an axial direction from a first ring at a proximal end followed by a plurality of succeeding rings to a final ring at a distal end. Each succeeding ring is preceded by a preceding ring. Each of the plurality of rings includes a plurality of adjacent peaks and valleys, wherein each valley is connected to an adjacent peak by a strut to provide an undulating pattern within each ring. Each of the plurality of rings has a compressed condition for delivery into the patient and an expanded condition after deployment in the patient, wherein, in the compressed condition each preceding ring has a preceding ring length measured in the axial direction and each succeeding ring has a succeeding ring length measured in the axial direction, wherein a ratio of each succeeding ring length divided by each preceding ring length is a constant number that is smaller than unity.

In some embodiments, the first ring has a first ring length and is connected to a second ring by a first link having a first link length, the first link length being equal to the first ring length. In further embodiment, the ratio is in a range of 0.90 to 0.95.

In yet a further embodiment, the invention is a method of expanding a stent within a vasculature of a patient. The method comprises disposing a stent upon a balloon that is deflated, the balloon comprising a center portion having a proximal end, a distal end opposite the proximal end, and a length between the proximal end and the distal end; inserting the balloon inside the vasculature of the patient; inflating the balloon to a nominal pressure and, simultaneously, imparting a cylindrical shape to the center portion of the balloon; and further inflating the balloon to a pressure beyond nominal pressure and, simultaneously, imparting a tapered shape to the center portion of the balloon. In some embodiments, imparting a cylindrical shape to the center portion of the balloon includes imparting a cylindrical shape to the stent. In further embodiments, imparting a tapered shape to the center portion of the balloon includes imparting a tapered shape to the stent.

These and other advantages of the invention will appear when read in conjunction with the description of the drawings and detailed description of some embodiments.

BRIEF DESCRIPTION OF THE DRAWINGS

FIG. 1A is a schematic view of a delivery catheter that is known in the art, tipped by a balloon at a distal end, upon which is mounted a stent.

FIG. 1B is a schematic view of a distal tip of the catheter of FIG. 1A, in the process of expanding the balloon for deployment in a vessel that tapers down in the distal direction.

FIG. 1C is a schematic view of a stent having a constant diameter known in the art that has been deployed in a vessel of a patient.

DETAILED DESCRIPTION OF SOME EMBODIMENTS

Figure 2:
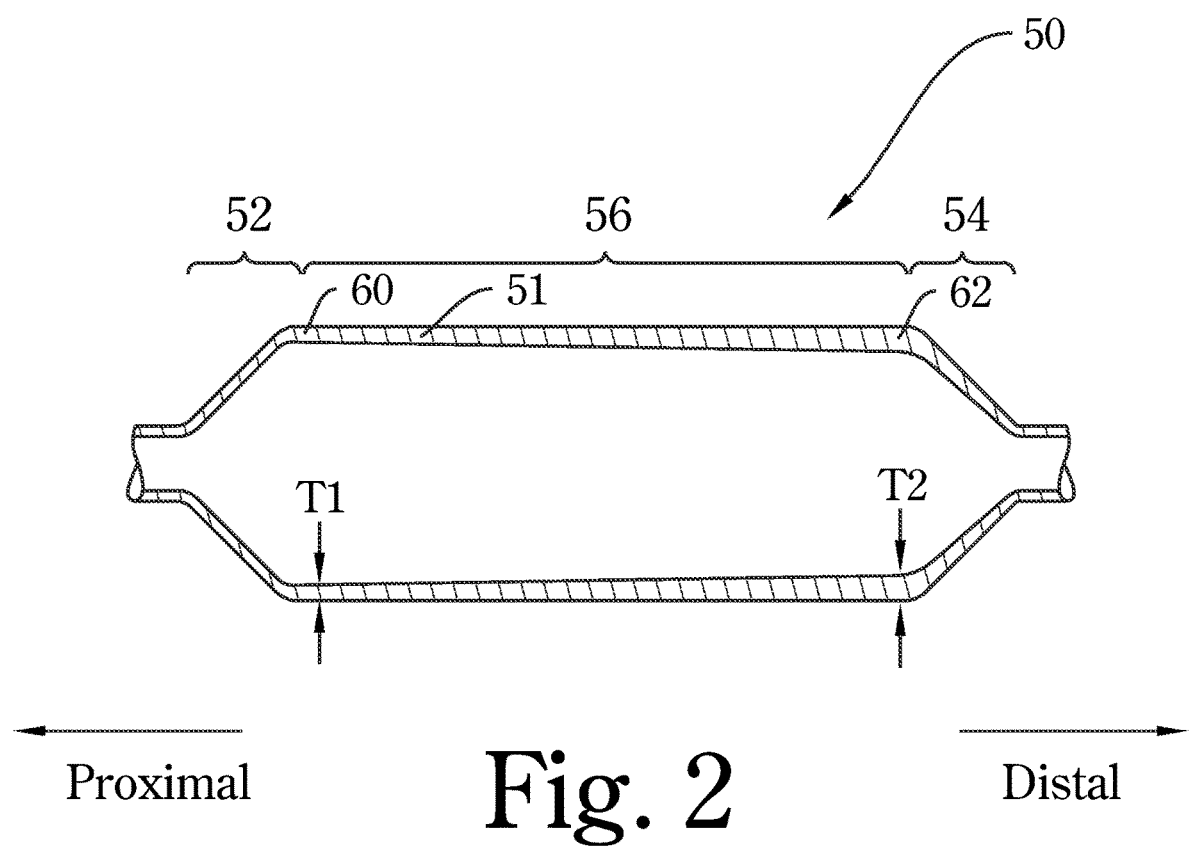
FIG. 2 is a schematic side elevational view of a first embodiment of a balloon having features of the invention.

Referring now to the drawings, wherein like reference numbers are used herein to designate like elements throughout, the various views and embodiments of a balloon configured for delivering a tapered stent are illustrated and described, and other possible embodiments are described.

The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 3:
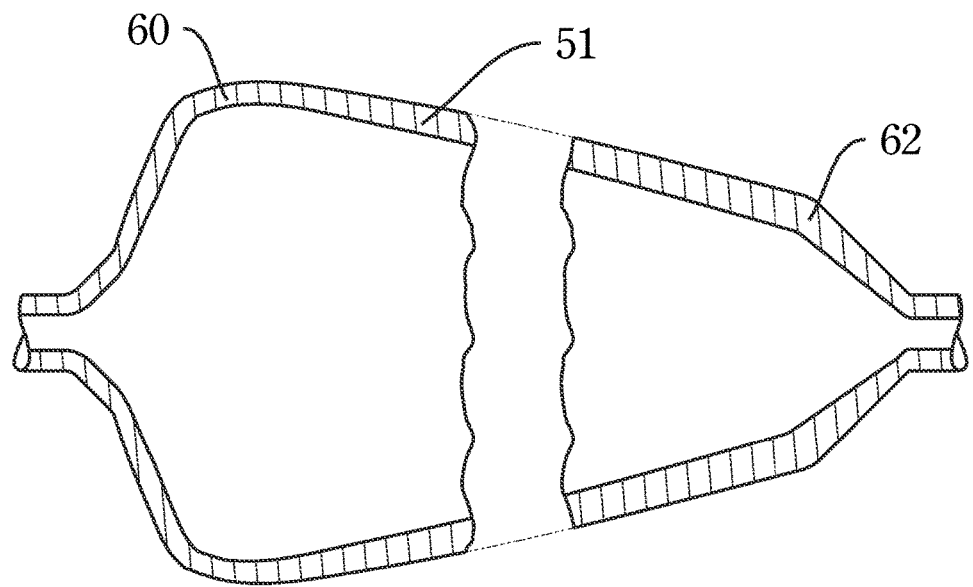
FIG. 3 is a sectional view of the embodiment of FIG. 2.

FIGS. 2-3 exemplify a first embodiment of the invention. FIG. 2 is a side sectional view of a balloon 50 configured for being fixed to the distal tip of a known catheter such as shown in FIG. 1A. The balloon 50 may be formed of a compliant membrane 51 formed of a suitable polymer material. A proximal section 52 of the balloon is configured to have an outwardly extending conical shape extending from the center towards the outer diameter of the balloon in the distal direction, and a distal section 54 configured to have an inwardly extending conical shape extending from the outer diameter of the balloon towards the center of the balloon in the distal direction. A central section 56, having a proximal end 60 and a distal end 62, joins the proximal section 52 to the distal section 54. The thickness of the membrane 51 is structured to have a thickness T1 at a first point where the proximal section 52 joins the central section 56, and a thickness T2 at a second point where the central section 56 joins the distal section 54. Importantly in this embodiment, T1 is thinner than T2. The thickness between the first point and the second point varies linearly between T1 and T2. (The membrane may be given this linearly varying thickness during the molding of the balloon by using an outer shaping mandrel with cylindrical internal bore surface, and an inner shaping mandrel with conical shaped exterior surface.) It will be understood that this configuration gives the balloon a higher radial modulus at the distal end, and a lower radial modulus at the proximal end. The term "radial modulus" means herein the amount of force that is needed to stretch the balloon membrane a certain amount in a radial direction. Because the pressure inside the balloon is the same at every point inside the balloon, the force applied inside the balloon, per unit length of the balloon, is the same at every point along the length of the balloon. Therefore, at a constant pressure when the balloon membrane is being stretched, the portion of the balloon having a higher radial modulus will stretch less than the portion of the balloon having the lower radial modulus. Accordingly, the higher radial modulus at the distant end of the balloon will cause the balloon at the distal end to stretch, radially, less than the balloon will stretch at the proximal end where the radial modulus is lower relative to the distal end.

The native balloon in this embodiment is initially formed to possess a constant uniform outer diameter over the central section 56 (as shown in FIG. 2) over its length at nominal pressure. ("Nominal pressure" is used herein to mean a pressure in the balloon that is sufficient to expand the balloon to remove all folds and wrinkles in the membrane 51 of the balloon, but not sufficient to place the membrane of the balloon under a tensile stress which is to say, it will not "stretch" the balloon membrane. The term "nominal diameter" of a balloon is used herein to mean a diameter that is achieved under nominal pressure.)

The result of this structural arrangement of the varying thickness of the balloon 50 may be understood with reference to FIGS. 2-3. Upon delivery of the balloon to the desired location within the vascular anatomy, the deflated balloon may be inflated to nominal pressure, which will cause the central section 56 of the balloon to achieve its constant diameter cylindrical shape along the length of the central section 56, as shown in FIG. 2, under which pressure the balloon membrane merely unfolds but does not begin to stretch. At this stage, the physician may assess, using known visualization techniques such as fluoroscopy, whether a satisfactory degree of apposition between the stent (not shown in FIG. 2) mounted on the balloon 50 and the vessel wall has been achieved in circumstances where the vessel may taper downward substantially towards the distal end. If the visualization shows that the taper of the vessel has left insufficient apposition at the proximal end, the physician may elect to continue to inflate the balloon to a higher pressure than nominal—under which circumstances the balloon membrane will begin to stretch. The result of such further inflation may be visualized by reference to FIG. 3, which shows the balloon 50 expanded to a larger diameter on the proximal end 60 than on the distal end 62, thereby imparting a distinct taper to the balloon over its length.

By relying on the emergence of this taper after nominal pressure has been reached and further inflation of the balloon is applied, the physician may elect to continue to inflate the balloon higher than nominal pressure, thereby improving the apposition of the stent over its length because it has been given a tapered profile to match the taper of the vessel.

Figure 4:
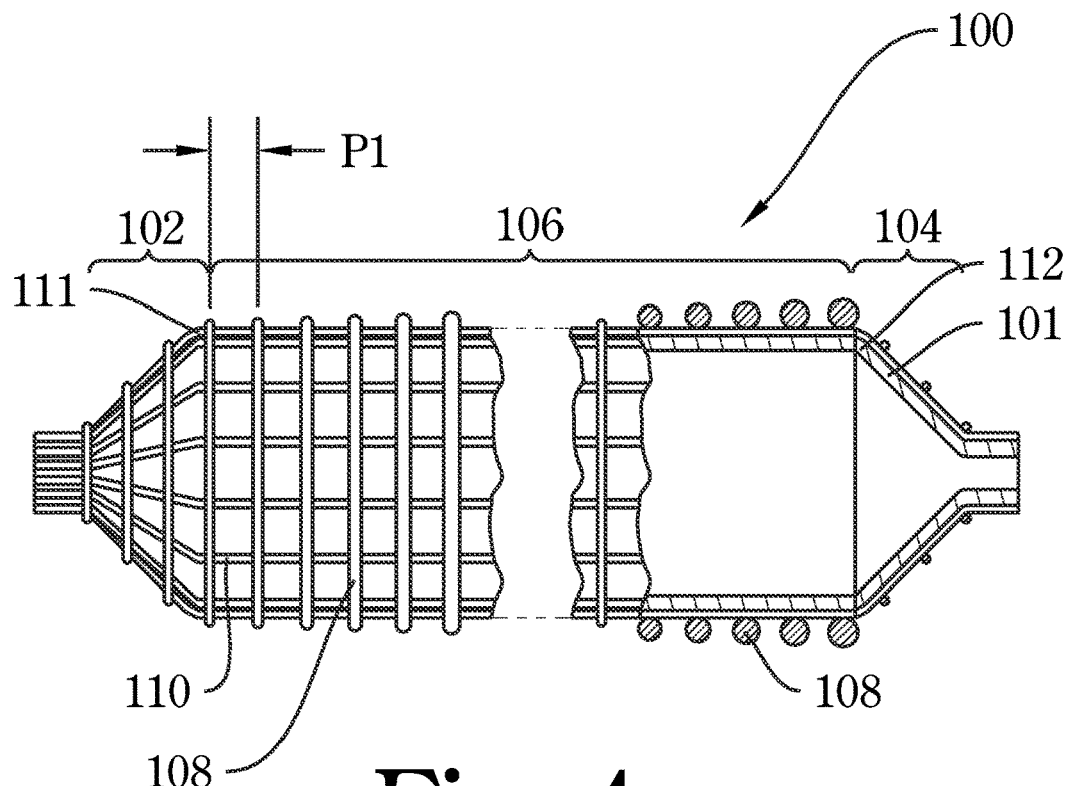
FIG. 4 is a schematic side elevational view of a second embodiment of a balloon having features of the invention.
Figure 5:
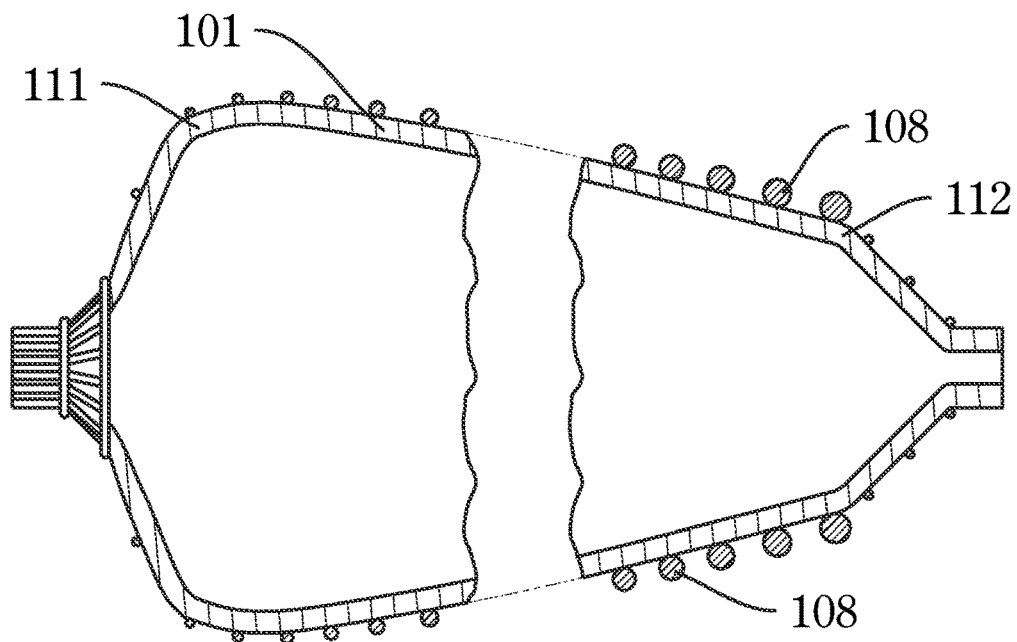
FIG. 5 is a sectional view of the embodiment of FIG. 4.

FIGS. 4-5 exemplify a second embodiment of the invention. FIG. 4 is a side elevational view, in partial cutaway section, of a balloon 100 configured for being fixed to the distal tip of a known catheter such as shown in FIG. 1. The balloon 100 may be formed of a compliant or semi-compliant membrane 101 formed of a suitable polymer material. A proximal section 102 of the balloon is configured to have an outwardly extending conical shape extending from the center towards the outer diameter of the balloon in the distal direction, and a distal section 104 configured to have a inwardly extending conical shape extending from the outer diameter of the balloon towards the center of the balloon in the distal direction. A central section 106, having a proximal end 111 and a distal end 112, joins the proximal section 102 to the distal section 104. The native balloon in this embodiment is initially formed to possess a constant uniform diameter over the central section 106 (as shown in FIG. 4) over its length at nominal pressure, and also a constant thickness of the membrane 101.

Further shown schematically are circumferential threads 108 that run circumferentially around the outside of the balloon to reinforce the balloon and add a controllable response to internal balloon pressure as will be described herein. These threads may either be annular in shape, and slipped over the balloon at a constant pitch P1 when the balloon is nominally inflated, or it may be wound around the balloon in a helical spiral having a constant pitch, when the balloon is nominally inflated. In either case, threads 108 may be attached to the surface of the balloon using a liquid adhesive, in known manner. In some embodiments, axial threads 110 may be applied and adhered to the outside of the balloon to extend horizontally, in order to reinforce and limit the expansion of the balloon along its longitudinal axis under inflation.

In the embodiment being described in FIGS. 4-5, the circumferential threads 108 may be selected to be compliant or semi compliant. To accomplish this objective, the threads may be made from a suitable polymer. In this embodiment, the circumferential threads are configured to have a diameter that increases as the threads move from the proximal end of the balloon (here, the left end of the balloon) to the distal end of the balloon (here, the right end). This effect may be envisaged by reference to FIGS. 4-5 where a schematic representation of gradually thickening threads 108 is shown. Where the threads are annuli affixed to the external surface of the balloon, each annulus may be formed to possess a slightly larger diameter than those adjacent, in an incrementally increasing fashion. Where the threads 108 comprise a single thread helically wound about the balloon, the diameter of the single thread increases from the proximal end to the distal end giving rise to the same effect, namely that the balloon is more rigidly constrained against radial expansion at the distal end, and less rigidly constrained against expansion at the proximal end. It will be understood that this configuration gives the balloon a higher radial modulus on average at the distal end, and a lower radial modulus on average at the proximal end.

The result of this structural arrangement of the threads 108 around the balloon may be understood with reference to FIGS. 4-5. Upon delivery of the balloon to the desired location within the vascular anatomy, the deflated balloon may be inflated to nominal pressure, which will cause the balloon to achieve its constant diameter cylindrical shape along its length, as shown in FIG. 4. At this stage, the physician may assess, using known visualization techniques such as fluoroscopy, whether a satisfactory degree of apposition between the stent (not shown in FIG. 4) and the vessel wall has been achieved in circumstances where the vessel tapers downward substantially towards the distal end. If the visualization shows that the taper of the vessel has left insufficient apposition at the proximal end, the physician may elect to continue to inflate the balloon to a higher pressure. The result of such further inflation may be visualized by reference to FIG. 5, which shows the balloon 100 expanded to a larger diameter on the proximal end 102 than on the distal end 104, thereby imparting a distinct taper to the balloon over its length. By relying on the emergence of this taper after nominal pressure has been reached and further inflation of the balloon is applied, the physician may elect to continue to inflate the balloon higher than nominal pressure, thereby improving the apposition of the stent over its length.

Figure 6:
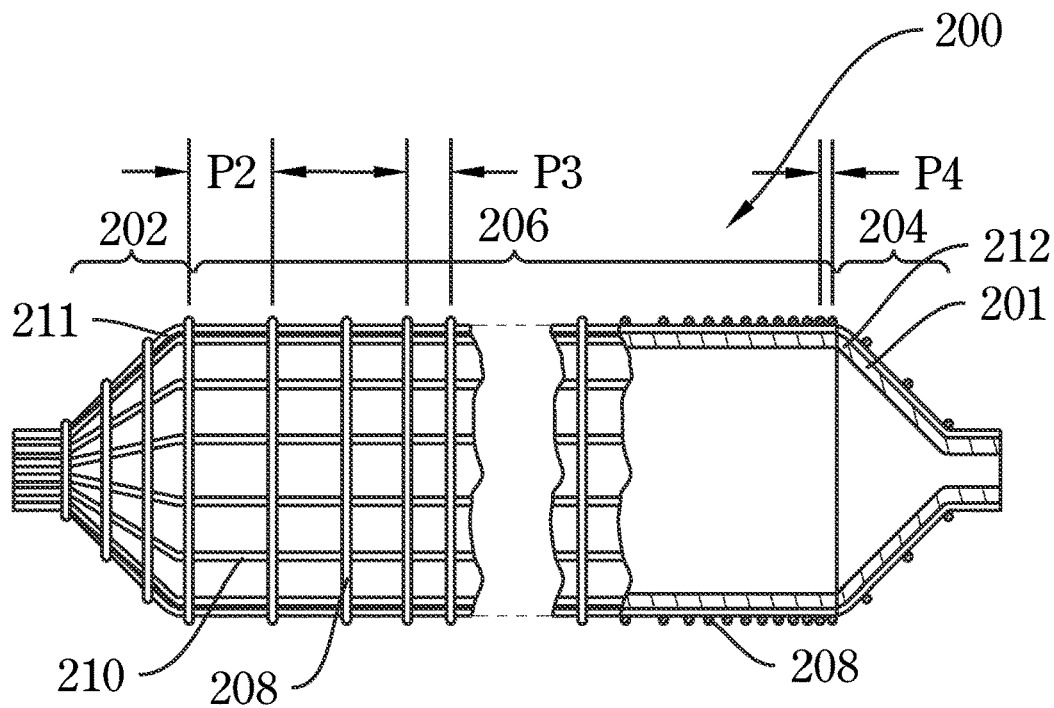
FIG. 6 is a schematic side elevational view of a third embodiment of a balloon having features of the invention.
Figure 7:
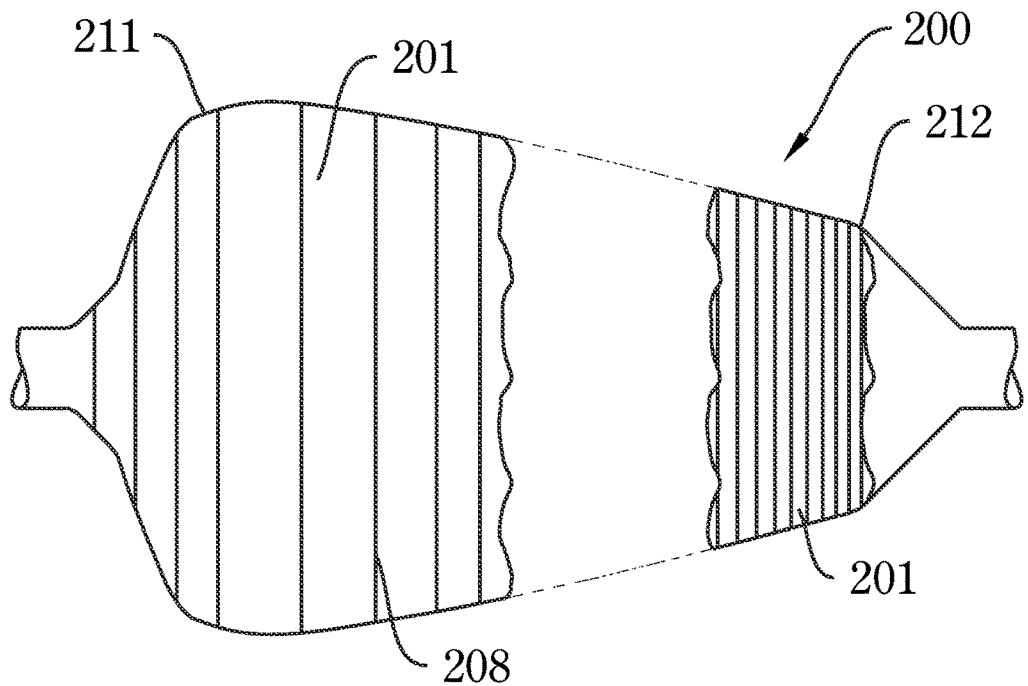
FIG. 7 is a sectional view of the embodiment of FIG. 6.

FIGS. 6-7 exemplify yet another embodiment of the invention, a balloon 200. The balloon 200 may be formed of a compliant membrane 201. A proximal section 202 of the balloon is configured to have an outwardly extending conical shape extending from the center towards the outer diameter of the balloon in the distal direction, and a distal section 204 configured to have an inwardly extending conical shape extending from the outer diameter of the balloon towards the center of the balloon in the distal direction. A central section 206, having a proximal end 211 and a distal end 212, joins the proximal section 202 to the distal section 204.

The underlying balloon membrane 201 here is the same as the membrane 101 in the previous embodiment. However, in this embodiment, the threads 208 around the balloon membrane have a constant diameter throughout the length of the balloon. Further, the threads 208 are in the form of annuli that are slipped onto and adhered to the external surface of the membrane at nominal pressure. In this embodiment, however, the pitch of the annuli does not remain constant. Rather, the pitch of the annuli start at a set pitch P2 on the proximal end of the balloon, the pitch gradually decreasing to a smaller pitch P4 at the distal end of the balloon via an intermediate size pitch P3 in the middle. This gives rise to the effect that the balloon is more rigidly constrained against radial expansion at the distal end, and less rigidly constrained against expansion at the proximal end. In other words, this configuration gives the balloon a higher radial modulus on average at the distal end, and a lower radial modulus on average at the proximal end. The advantage of this arrangement has been described and explained above with respect to the embodiment in FIGS. 4-5, and is no less advantageous.

Figure 8:
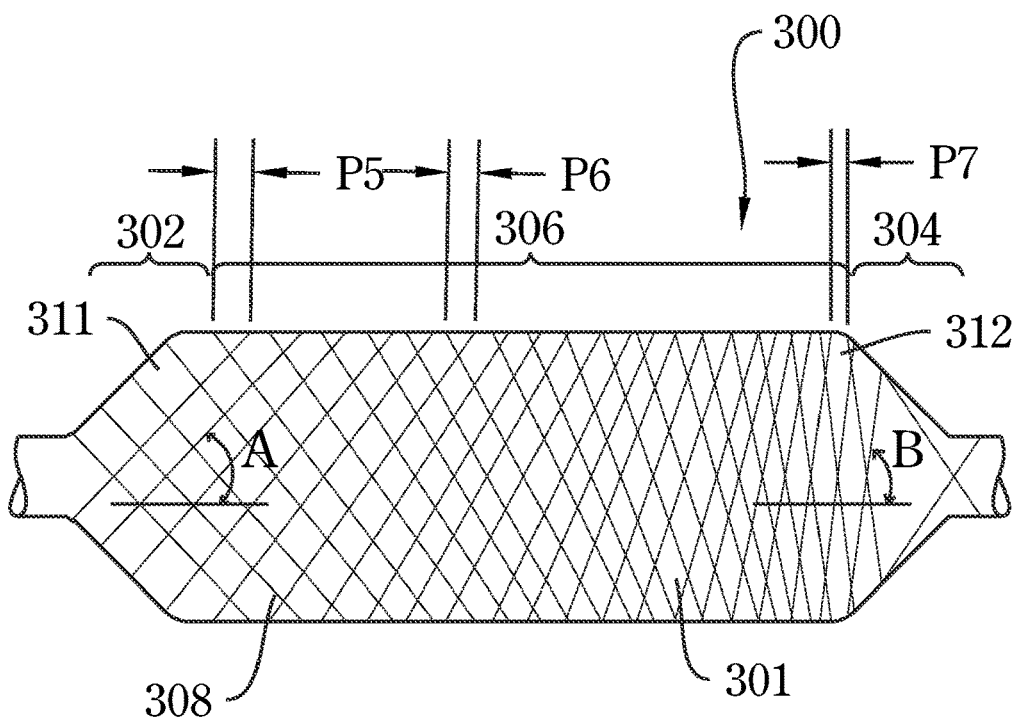
FIG. 8 is a schematic side elevational view of a fourth embodiment of a balloon having features of the invention.
Figure 9:
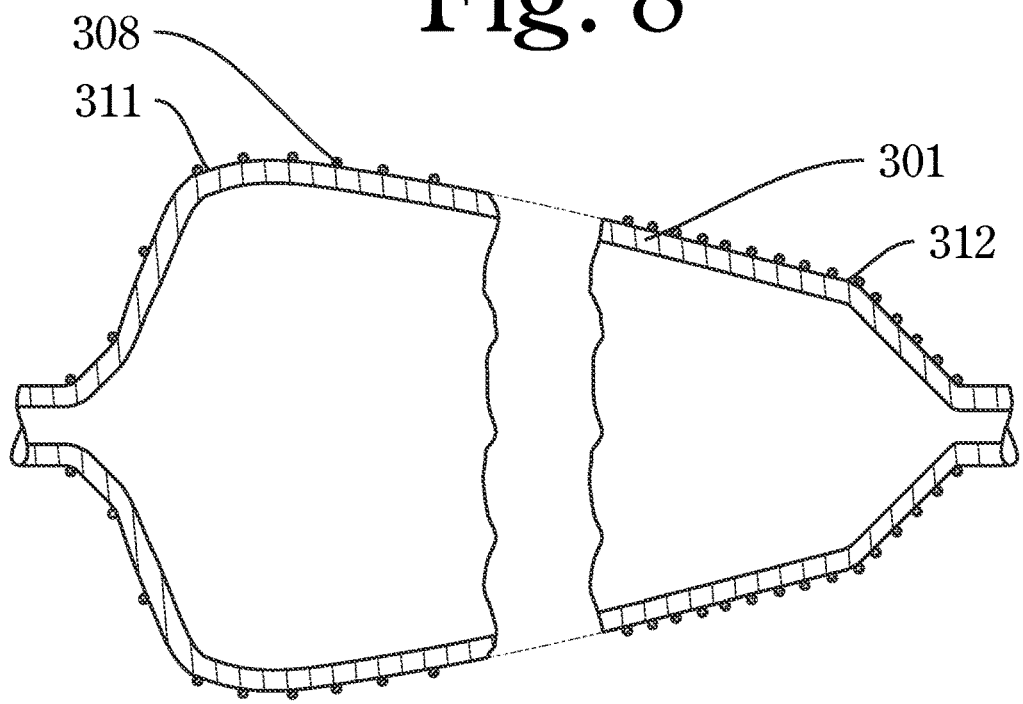
FIG. 9 is a sectional view of the embodiment of FIG. 8.

FIGS. 8-9 exemplify yet another embodiment of the invention, balloon 300. The balloon 300 may also be formed of a compliant membrane 301. A proximal section 302 of the balloon is configured to have an outwardly extending conical shape extending from the center towards the outer diameter of the balloon in the distal direction, and a distal section 304 configured to have an inwardly extending conical shape extending from the outer diameter of the balloon towards the center of the balloon in the distal direction. A central section 306, having a proximal end 311 and a distal end 312, joins the proximal section 302 to the distal section 304.

The underlying balloon membrane 301 here is the same as the membrane 101 above. However, in this embodiment, the threads 308 around the balloon membrane have a constant diameter throughout the length of the balloon. Further, the threads 308 are in the form of a single thread wound around the exterior of the membrane 301 at nominal pressure. In this embodiment, however, the pitch of the single wound threads 308 has a helical pitch that starts at a set pitch P5 on the proximal end of the balloon, the pitch gradually decreasing to a smaller pitch P7 at the distal end of the balloon with an intermediate pitch P6 in the middle. It will be appreciated that, as the pitch moves to a smaller amount, the angle of each thread changes from a shallow angle A to a steep angle B. This gives rise to the effect that the balloon is more rigidly constrained against radial expansion at the distal end, and less rigidly constrained against expansion at the proximal end. In other words, this configuration gives the balloon a higher radial modulus on average at the distal end, and a lower radial modulus on average at the proximal end.

The advantage of this arrangement has been described and explained above with respect to the embodiment in FIGS. 4-5, and is no less advantageous.

Figure 10:
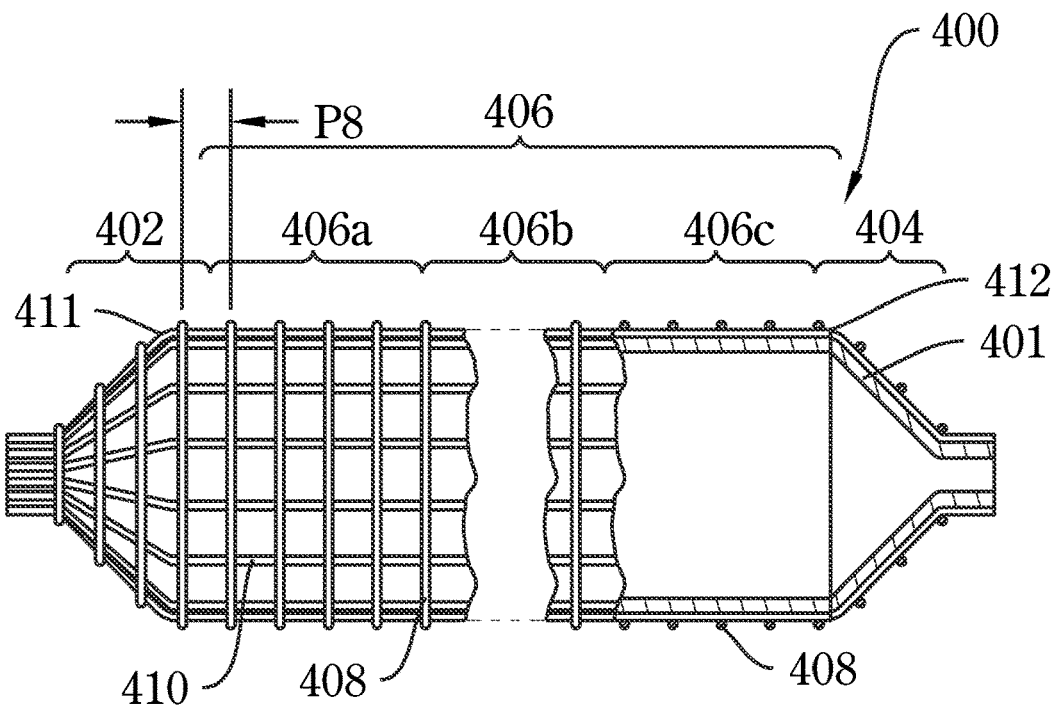
FIG. 10 is a schematic side elevational view of a fifth embodiment of a balloon having features of the invention.
Figure 11:
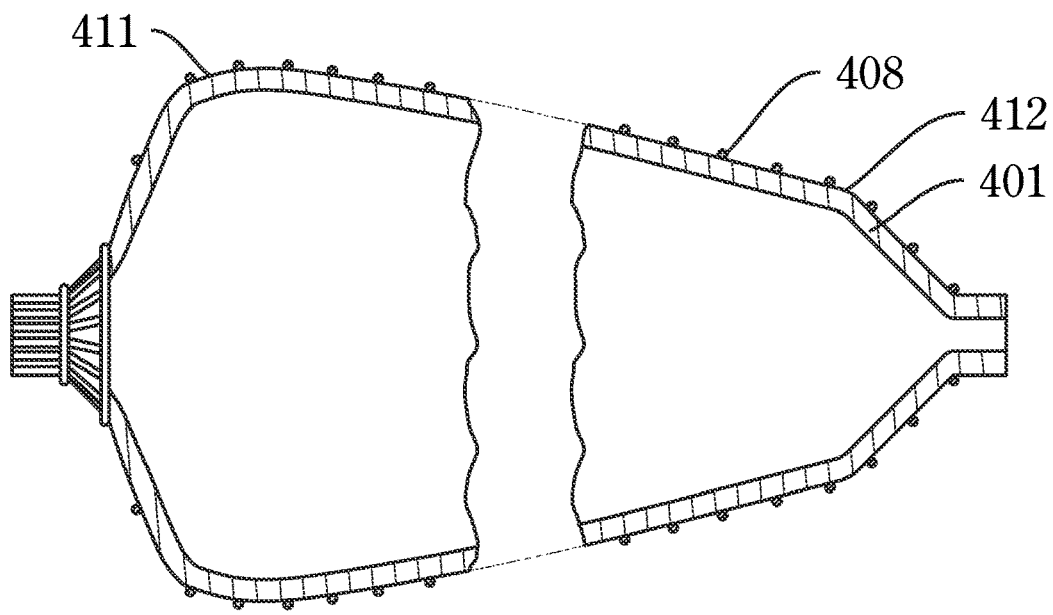
FIG. 11 is a sectional view of the embodiment of FIG. 10.

FIGS. 10-11 exemplify yet another embodiment of the invention, balloon 400. The underlying balloon membrane 401 here is the same as the membrane 101 above. The balloon 400 may also be formed of a compliant membrane 401. A proximal section 402 of the balloon is configured to have an outwardly extending conical shape extending from the center towards the outer diameter of the balloon in the distal direction, and a distal section 404 configured to have an inwardly extending conical shape extending from the outer diameter of the balloon towards the center of the balloon in the distal direction. A central section 406, having a proximal end 411 and a distal end 412, joins the proximal section 402 to the distal section 404.

However, in this embodiment, the threads 408 around the balloon membrane have been selected to possess a constantly changing elastic modulus. In this embodiment, the pitch of the annuli may remain constant at a pitch of P8. Under this embodiment, the center portion 406 of the balloon is divided into sub zones, for example proximal zone 406a, center zone 406b, and distal zone 406c. It will be appreciated that three zones are exemplary, and that more than, or fewer than, three zones may be used. In the proximal zone 406a, the threads 408 are selected for having a highly compliant modulus of elasticity, and may be made from a suitable polymer. In the center zone 406b, the threads are selected for having a semi-compliant modulus of elasticity, and may be made from a suitable polymer. In the distal zone 406c, the threads are selected for having a non-compliant modulus of elasticity, and may be made from a suitable polymer. It will be appreciated that, if the designer wishes to achieve a smoother transition of elasticities along the length of the balloon, then the threads may be made a mixture of the identified materials, with a stronger admixture of non-compliant material being added as the threads are added towards the distal end. This structural arrangement gives rise to the effect that the balloon 403 is more rigidly constrained against radial expansion at the distal end, and less rigidly constrained against expansion at the proximal end. In other words, this configuration gives the balloon a higher radial modulus on average at the distal end, and a lower radial modulus on average at the proximal end.

The advantage of this arrangement has been described and explained above with respect to the embodiment in FIGS. 4-5, and is no less advantageous.

Thus, a number of balloon embodiments are described that produce a balloon that adopts a constant cylindrical diameter at nominal pressure, but that adopts a tapering form at pressures above nominal.

Turning now to a stent configuration that is highly appropriate for use in combination with the balloon embodiments that have been described, the stent configuration is described with reference to FIGS. 12 and 13.

Figure 12:
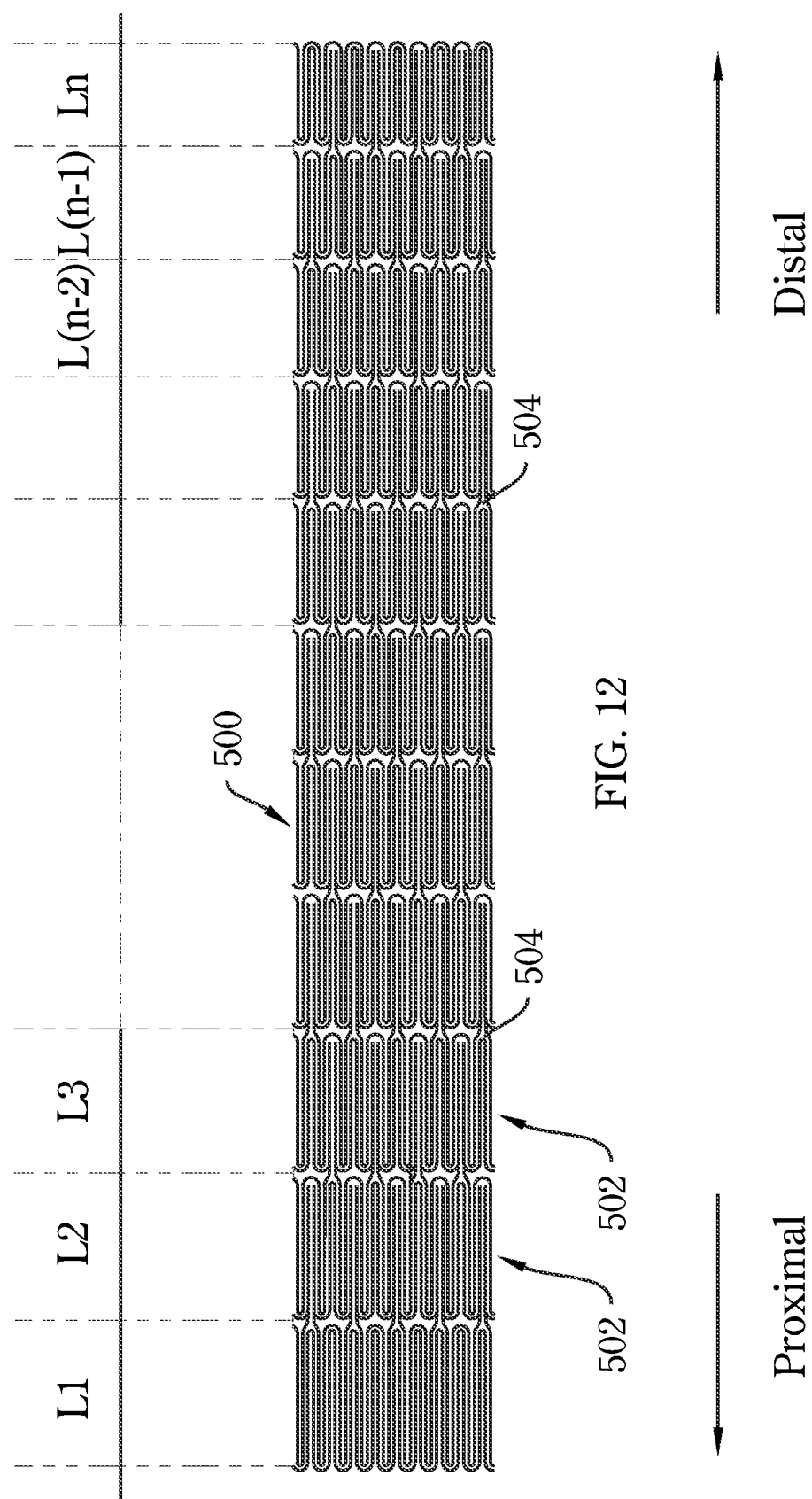
FIG. 12 is a "rollout" view of a stent, in unexpanded condition, suitable for use with any embodiment of the balloons in FIGS. 2-11.
Figure 13:
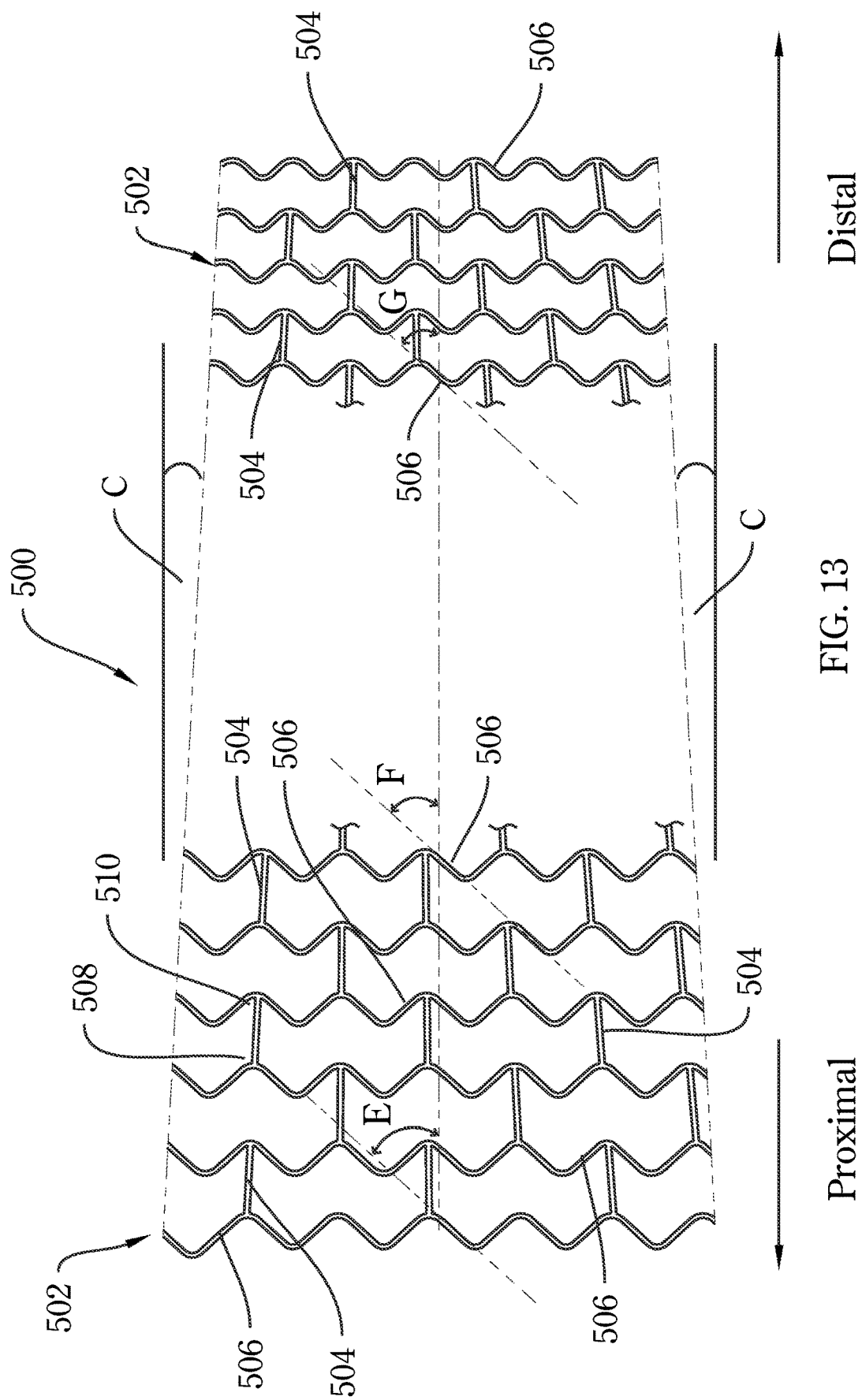
FIG. 13 is a "rollout" view of the stent shown in FIG. 12, in expanded condition.

FIG. 12 is a "rollout view" of a stent 500 having features of an embodiment of the invention in a condition before it is deployed (compressed or crimped condition) and FIG. 13 shows the same stent in a rollout condition after it is deployed (expanded condition). The form of the stent is one of a "ring and link" structure, in which short cylindrical rings 502 are connected to each other by links 504 extending parallel with the elongate axis of the stent. Each ring 502 is formed by a series of peaks 508 and valleys 510 that are connected to each other by arms 506 to provide a ring that extends the circumference of a cylinder while adopting an oscillating or wave-like shape. Peaks 508 on one ring are connected to valleys 510 of an adjacent ring to make up the stent, which has a great amount of flexibility in the longitudinal direction.

Of significance in the present invention, however, is that the axial length of each ring 502 in the compressed condition decreases from the proximal end towards the distal end. This is understood with reference to FIG. 12, where there is shown a stent having "n" rings along its length. The first ring on the proximal end has a length L1, the second ring has a length L2, and on . . . to the nth ring at the distal end which has a length Ln. As shown in FIG. 12, the length of L1 is longer than L2, which is longer than L3, . . . all the way to Ln which has the shortest length. In a preferred embodiment, the rate at which the rings shorten in length is constant, by which it is meant that the ratio of the length of any ring to the length of the preceding ring is a constant number. Thus, for example, if there are "n" rings, the length of the first ring is L1, and the ratio of L2/L1 is 0.95, then the length of the "nth" ring Ln will be L1 $(0.95)^{n-1}$ and, in a practical example, if n=10, then the "nth" ring will have length L1*0.63, or stated otherwise, 63% of L1, with the length of the intermediate rings being evenly distributed between L1 and L1*0.63 in length.

The structure shown in FIG. 12 may be cut from a cylinder having a constant diameter over its length and a constant thickness, according to known means by laser energy. The number of peaks and valleys are preferably the same in each ring 502, and the number of links 504 are the same between each ring. The only aspect that varies from ring to ring is the length of each ring. Preferably, the length of each link may also vary, in order to allow the spacing between the rings to remain constant.

The advantage provided by the structure described above is that the stent 500 will, upon expansion by a balloon, be capable of adopting a configuration such as is shown in FIG. 13, in which each ring is expanded to a similar degree, yet the stent will have a gradual taper from the proximal end narrowing to the distal end. The term "similar degree" to describe expansion of a ring indicates that when two rings are expanded to a "similar degree," then each arm 506 of each ring will be angled at substantially the same angle to the elongate axis of the stent. For example, the angles shown as E, F, G in FIG. 13 are all substantially equal to each other, and reflect the fact that the rings identified are expanded to a similar degree to each other. This geometric consequence follows necessarily from the fact that, according to the geometry of the rings, the proximal rings have a longer length than the distal rings. It will be appreciated by one of ordinary skill that a stent in which all the rings are expanded to a "similar degree" will possess expanded rings that possess similar radial strength to each other. This is a desirable outcome, and has an advantage over a stent with identical rings that is deformed into a tapered shape, because in such a stent the rings will be expanded to different degrees, and will possess different radial strength from each other.

It will be appreciated that the stent described in reference to FIGS. 12-13 will benefit from the balloon embodiments that have been described. The balloon embodiments are capable of providing a balloon that can be shaped with a relatively precise taper after the balloon passes beyond nominal pressure. Further, the stent may be cut so that it also will expand with a relatively precise taper, while at the same time possessing a uniform and constant radial strength along its length.

Thus, the balloons and stent of the present invention provide an advantageous structure and method for improving the apposition of stents within tapered vessels. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A method of expanding a stent within a vasculature of a patient comprising:
   disposing the stent upon a balloon that is deflated,
   wherein: the stent comprises
      a plurality of rings that are successively connected to each other by a plurality of links,
      the plurality of rings extending in an axial direction from a first ring at a proximal end followed by a plurality of succeeding rings to a final ring at a distal end, wherein, each succeeding ring is preceded by a preceding ring;
      each of the plurality of rings includes a plurality of adjacent peaks and valleys, wherein each valley is connected to an adjacent peak by an arm to provide an undulating pattern within each ring; and
      each preceding ring has a first number of peaks and each succeeding ring has a second number of peaks, the first number being equal to the second number;
      each of the plurality of rings has a compressed condition for delivery into the patient and an expanded condition after deployment in the patient, wherein,
      in the compressed condition each preceding ring has a preceding ring length measured in the axial direction and each succeeding ring has a succeeding ring length measured in the axial direction, wherein a ratio of each succeeding ring length divided by each preceding ring length is a constant number that is smaller than unity;

wherein the balloon comprises
- a center portion having a proximal end, a distal end opposite the proximal end, and a length between the proximal end and the distal end, wherein the center portion further comprises:
- a first nominal diameter and a first radial modulus at the proximal end;
- a second nominal diameter and a second radial modulus at the distal end;
- wherein, the first nominal diameter is equal to the second nominal diameter, such that, when the balloon is inflated to a nominal pressure, the center portion has a constant diameter over the length; and further wherein,
- the first radial modulus is smaller than the second radial modulus, such that, when the balloon is inflated above a nominal pressure, the center portion adopts a tapered shape in which the proximal end has a first stretched diameter and the distal end has a second stretched diameter, the first stretched diameter being larger than the second stretched diameter;

inserting the balloon and the stent disposed thereon, inside the vasculature of the patient;

inflating the balloon to a nominal pressure, imparting a cylindrical shape to the center portion of the balloon and, simultaneously, imparting a cylindrical shape to the stent; then assessing whether suitable apposition between the stent and the vasculature has been achieved and then further inflating the balloon to a pressure beyond nominal pressure, imparting a tapered shape to the center portion of the balloon and, simultaneously, imparting a tapered shape to the stent.

2. The method of claim 1, wherein, imparting a tapered shape to the stent includes expanding each of the rings of the stent to a similar degree whereby each arm of each ring is angled at the same angle to an elongate axis of the stent.

* * * * *